(12) United States Patent
Wollmann et al.

(10) Patent No.: US 6,956,125 B2
(45) Date of Patent: Oct. 18, 2005

(54) PROCESSES FOR PRODUCING STEROLS FROM FATTY ACID PRODUCTION RESIDUES

(75) Inventors: Gerhard Wollmann, Hilden (DE); Joerg Schwarzer, Hilden (DE); Bernhard Gutsche, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 544 days.

(21) Appl. No.: 09/923,629

(22) Filed: Aug. 7, 2001

(65) Prior Publication Data

US 2002/0058827 A1 May 16, 2002

(30) Foreign Application Priority Data

Aug. 7, 2000 (DE) .......................................... 100 38 442

(51) Int. Cl.$^7$ ................................................. C07J 9/00
(52) U.S. Cl. ....................................................... 552/545
(58) Field of Search ......................................... 552/545

(56) References Cited

U.S. PATENT DOCUMENTS

| | | | |
|---|---|---|---|
| 4,148,810 A | 4/1979 | Struve | |
| 5,487,817 A | 1/1996 | Fizet | |
| 5,514,820 A | 5/1996 | Assmann et al. | |
| 5,627,289 A | 5/1997 | Jeromin et al. | |
| 5,670,669 A | * 9/1997 | Hunt | 549/413 |
| 5,703,252 A | * 12/1997 | Hunt et al. | 549/413 |
| 6,448,423 B1 | * 9/2002 | Hernandez et al. | 554/197 |

FOREIGN PATENT DOCUMENTS

| | | |
|---|---|---|
| DE | 42 28 476 A1 | 3/1994 |
| DE | 199 16 034 C1 | 8/2000 |
| EP | 0 333 472 A2 | 9/1989 |
| EP | 0 610 742 A1 | 8/1994 |
| EP | 0 494 177 B1 | 3/1996 |
| EP | 0 656 894 B1 | 2/1998 |
| GB | 2 145 079 A | 3/1985 |

* cited by examiner

*Primary Examiner*—Barbara P. Badio
(74) *Attorney, Agent, or Firm*—John F. Daniels

(57) ABSTRACT

The invention relates to a process for the production of sterols from fatty acid distillation residues, characterized in that the partial glycerides are subjected to a first transesterification step under mild conditions and, after working up and the removal of impurities, the sterol esters are subjected to a second transesterification step under more extreme conditions.

32 Claims, No Drawings

PROCESSES FOR PRODUCING STEROLS FROM FATTY ACID PRODUCTION RESIDUES

BACKGROUND OF THE INVENTION

The production of sterols from distillates obtained in the deacidification of vegetable oils or from distillation residues accumulating in the production of methyl esters and more particularly in the production of methyl esters from crops for "biodiesel" applications is generally known.

One known process for the production of sterols has been described wherein a residue from the distillation of methyl esters essentially consisting of glycerides, sterols, sterol esters and tocopherols is transesterified with methanol in the presence of alkaline catalysts. However, the sterol yield is unsatisfactory. Although some improvements have been made, including the utilization and revaluation of residues from the production of fats and oils and their constituents, such improvements can involve costly, elaborate processes using ecologically harmful solvents. For example, in some processes readily volatile sterols from the distillation residues of fat and oil production and working up are isolated by transesterification and subsequent dissolution in aprotic organic solvents.

Accordingly, the problem addressed by the present invention was to produce sterols in high yields and high purity by an economic process that would avoid toxicologically and ecologically unsafe solvents and, at the same time, to utilize residues from fatty acid production more economically.

SUMMARY OF THE INVENTION

This invention relates generally to sterol production and more particularly to a process for the production of sterols from residues from fatty acid production.

The present invention relates to a process for the production of sterols which comprises: (a) providing a fatty acid production-residue, said residue comprising sterol esters, free fatty acids, and partial glycerides; (b) removing the free fatty acids; (c) transesterifying the partial glycerides with a lower alcohol in the presence of a basic catalyst under mild transesterification conditions to form fatty acid alkyl esters and glycerol; (d) removing excess lower alcohol, the basic catalyst, the glycerol and the fatty acid alkyl esters, to form a bottom product comprising the sterol esters; and (e) transesterifying the sterol esters at a temperature of from 115° C. to 145° C. and a pressure of from 2 to 10 bar for a period of from 3 to 10 hours to form free sterols.

A preferred embodiment of the present invention is directed to a process for the production of sterols from the residues of fatty acid production, in which (a) free fatty acids present in the residues are esterified by polyolysis or with a lower alcohol, (b) the partial glycerides present in the mixture are transesterified with a lower alcohol in the presence of a basic catalyst for 2 to 20 minutes at temperatures of 90 to 145° C. and under a pressure of 2 to 10 bar, (c) the excess lower alcohol is distilled off from the reaction mixture after the transesterification, (d) the transesterification catalyst and the glycerol present, if any, are removed, (e) the fatty acid alkyl ester is distilled off from the mixture and (f) the sterol esters and residual partial glycerides present in the bottom product are converted into free sterols and fatty acid esters by further transesterification for 4 to 8 hours at temperatures of 115 to 145° C. and under a pressure of 2 to 10 bar.

It has been found that the residues from fatty acid production still contain high-quality sterols which can be economically recovered without harming the environment by a process in which one esterification step is combined with two transesterification steps. In a first transesterification step (b), the mono-, di- and triglycerides present after the esterification of the free fatty acids present in the residues are reacted under mild conditions with a lower alcohol in the presence of a basic catalyst. Under the mild conditions, the sterol esters remain predominantly bound and only a small amount of free sterols is formed (<1% by weight). The first transesterification step proceeds very quickly and saves time so that it can be carried out in a simple tube reactor.

After removal of the excess alcohol, transesterification catalyst and glycerol, the free methyl esters are distilled, resulting in concentration of the sterol esters at the bottom of the column. The sterol esters are then transesterified into the free sterols in a second transesterification step (f) carried out under more extreme conditions. By virtue of the fact that the impurities, such as fatty acid, methyl ester and glycerol, are removed in this transesterification step and the sterol esters are present in concentrated form, the free sterols can be obtained under far more economic conditions.

After the second transesterification step, the free sterols are crystallized and washed. They may then be melted and solidified into dust-free spherical particles by spraying through droplet-forming nozzles into a gravity tower and cooling with air flowing in countercurrent.

The process is suitable for various starting mixtures. High-quality yields are achieved. The additional utilization of the distillation residues leads to an economic, ecologically safe process that is easy to carry out on an industrial scale.

DETAILED DESCRIPTION OF THE INVENTION

Residues from Fatty Acid Production

Studies of fatty acid production have shown that the distillation residues of fatty acid production still contain high-quality sterols, mainly in the form of sterol esters. Residues from the production of soya, sunflower and rapeseed oil fatty acids are particularly suitable because the oils have a higher starting concentration of sterols. With additional outlay, however, distillation residues from the production of coconut, palm or palm kernel oil fatty acids may also be used.

Free or even bound sterols are insoluble in water and, after the splitting of the fats and oils which mainly takes place at 250–260° C./50–60 bar in the absence of a catalyst, are present together with the split fatty acid and the unsplit partial glycerides. In the production of the free fatty acids, the fatty acids are then normally subjected to overhead distillation optionally coupled with fractionation (G. Dieckelmann, I. J. Heinz, The Basics of Industrial Oleochemistry (1988, pages 52 et seq)). The free sterols undergo at least partial autocatalytic esterification with free fatty acids to form sterol esters; partial glycerides and traces of free glycerol are also reacted. The severe heat stress involved in the fat-splitting and working-up steps does not cause any reduction in the quality of the sterols.

In spite of this, the residues accumulating in the production of vegetable fatty acids are normally used as an animal feed. Accordingly, the recovery of the sterols accumulating therein represents a better and more economic utilization of the raw material sources.

Typical concentrations of free and bound sterols in the fatty acid distillation residues are:

| | |
|---|---|
| from soybean oil: | 5 to 20% by weight |
| from sunflower oil: | 5 to 25% by weight |
| from rapeseed oil: | 5 to 30% by weight |
| from coconut/palm kernel oil: | 5 to 15% by weight |
| from palm oil: | 3 to 10% by weight |

Processes for Working Up a Distillation Residue Before the First Transesterification Step
Use of Residues Containing Residual Fatty Acids for Sterol Production, Esterification;

Fatty-acid-containing residues from the distillation of split fats and oils with an acid value of 20 to 100 and preferably 30 to 50 are used in a first esterification step according to the invention. These residues are in particular residues from the splitting of soybean oil, sunflower oil, rapeseed oil and coconut oil. However, residues from the processing of palm oil, palm kernel oil, cottonseed oil, corn oil or coconut oil may also be used.

According to the invention, the residual fatty acids in the residues are first esterified or removed. Suitable esterification processes are (i) polyolysis with a polyhydric short-chain alcohol, and (ii) esterification with a monohydric alcohol; the monohydric alcohol subsequently used in the transesterification is particularly preferred.

According to the invention, the esterification process is preferably a polyolysis. Glycerol is preferably used as the polyol. Polyolysis with glycerol takes place at elevated temperatures of 180 to 230° C. with or without a catalyst. Any esterification catalyst may be used for the polyolysis. In the catalyzed process, a divalent tin catalyst, for example tin oxide, tin oxalate, tin octoate and tin chloride, is preferably used in a quantity of 0.1 to 1% by weight and more particularly 0.2 to 0.4% by weight. However, the non-catalyzed variant is preferred.

The same molar quantity of glycerol as fatty acids present is preferably used. Monoglycerides are thus preferably formed in the case of glycerolysis. A high reaction rate, i.e. a short reaction time, is achieved in this way, even without a catalyst. The water formed during the reaction is distilled off. In order to obtain a high conversion, the reaction is carried out at final temperatures of 215 to 230° C. The pressure is reduced from an initial 1 bar to 5 mbar. Residual acid values of 0.5 to 2.5 are desirable.

By polyolysis with glycerol, the fatty acids are converted into relatively high-boiling partial glycerides. This has the advantage that non-reactable, unsaponifiable fractions can be selectively removed towards the end of the reaction by distillation in vacuo, for example, at from 1 to 10 mbar.

Alternatively, any esterification process by which the acid value can be reduced to below 4 may be used. Such processes include, for example, (i) homogeneous esterification of the residual fatty acids with alcohol, for example methanol, ethanol, butanol, hexanol, in the presence of an esterification catalyst such as, for example, NaHSO4, zinc soaps, phosphorous acids H3PO3, phosphoric acid H3PO4, P2O5, p-toluenesulfonic acid, alkyl benzenesulfonic acid, Ca acetate, Ba acetate; (ii) homogeneous esterification of the residual fatty acids with polyols, for example trimethylol propane, pentaerythritol, in the absence of a catalyst and/or with an esterification catalyst such as, for example, divalent tin catalysts (see above); and (iii) heterogeneous esterification of the residual fatty acids with a monohydric alcohol, for example methanol, ethanol, butanol, hexanol or polyols, on a catalytically active fixed bed, for example with acidic ion exchangers.

The residual fatty acid still present and the catalyst are optionally removed after polyolysis or esterification by any of the processes mentioned above. The residual fatty acid is neutralized, for example with a sodium metasilicate in which $Na_2O$ is bound and the catalyst is precipitated. The sodium metasilicate commercially available as Simet-AP (CAS 6834-92-0) is preferably used in a quantity proportional to the residual acid value (quantity of Simet=acid value g/kg product). The Simet/soap complex is removed by filtration or centrifugation.

First Transesterification Step

In the "mild transesterification of the partial glycerides" process step, glycerides are used with sterol esters having a low acid value. In a preferred embodiment, only the tri-, di and monoglycerides are reacted with a short-chain alcohol, preferably methanol or ethanol, under relatively mild conditions to form methyl ester and glycerol. Under the mild conditions, the sterol esters remain substantially bound. Only a small amount of free sterols is formed (less than 1%).

The starting material used for the transesterification of the partial glycerides comprises; the reaction products of the "polyolysis of free fatty acids" by the process mentioned above, the reaction products of the "esterification of free fatty acids" by any of the processes mentioned above, and any partial glycerides present in the original residue.

The raw materials used are distillation residues from the production of soybean oil, sunflower oil, rapeseed oil, coconut oil, palm kernel oil, corn oil, cottonseed oil or palm oil fatty acids or mixtures thereof Methanol containing 15 to 30% by weight of the residue is preferably used as the alcohol for the mild esterification. Any transesterification catalyst may be used as the catalyst. 30% by weight methanolic sodium methylate solution containing 0.1 to 0.5% by weight of the residue is preferably used.

The transesterification reaction takes place under mild conditions which may be established through the reaction temperatures or through the reaction time. Preferred conditions are temperatures T of 90 to 145° C., pressures p of 2 to 10 bar and more particularly 3 to 5 bar and reaction times of 2 to 20 minutes. Suitable reactors are stirred batch autoclaves and continuous reactors such as, for example, turbulent flow tube reactors (EP 0 494 177 B1).

Working-up Between the First and Second Transesterification Steps:
Distilling Off the Lower Alcohol (Preferably Methanol)

In the "distilling off the excess methanol" process step, the hot reaction mixture from step b) is expanded into a receiver, 55 to 85% of the excess methanol distilling off. The system cools down to 65–85° C. The residual methanol still left in the reaction product is preferably not distilled off and serves as solubilizer in the following stage.

Water is preferably introduced into the system before or during "flashing" in order to inactivate the alkaline catalyst. In molar terms, as much water is preferably present as alkaline catalyst was used.

Catalyst Precipitation and Removal of the Metals (d)

The raw materials, for example the fatty acid distillation residues, still contain metals, such as calcium (40–100 ppm), iron (20–1000 ppm), phosphorus (up to 15 ppm). The reaction products of the "esterification of free fatty acids" still contain esterification catalysts; after the catalyzed polyolysis, preferably divalent tin compounds. These catalyst soaps are soluble in the reaction mixture of the first transesterification. In order to be able to remove them, they are converted into insoluble compounds with acids and precipitated in accordance with the invention. Aqueous solutions of citric acid or phosphoric acid are preferably used as the acids. The quantity of acid used is preferably once to twice the molar concentration of metal.

After precipitation, the metal-containing sludge precipitated is removed by centrifuging and washing out with water. Alternatively, the precipitated metals are adsorbed. Suitable adsorbents are amorphous silica gels charged with organic acids such as, for example, Trysil types (Grace). Residual metal contents of 0 to 6 ppm are obtained.

Alternatively, precipitation of the metals and removal from fatty acid distillation residues is carried out directly after the non-catalyzed polyolysis together with removal of the Simet/soap complex by filtration or centrifuging.

Removal of Glycerol and Washing (d)

The glycerol is then removed, for example by decantation. Alternatively, the free glycerol and the residual methanol are washed out from the reaction product with water (two to three times 10% by weight water per reaction product) in the presence of citric acid for demulsification. The product is then dried.

Fatty Acid Alkyl Ester Distillation (e)

To concentrate the sterol esters, the alkyl (preferably methyl) ester is distilled off at temperatures of 170 to 200° C. and under pressures of 1 to 5 mbar. According to the invention, it was essentially only the partial glycerides that were transesterified in the "mild transesterification of the partial glycerides" process step. Since the sterols are still largely present as sterol esters, they are higher boiling and are not distilled off during distillation of the methyl ester. According to the invention, they remain entirely as a concentrated valuable product in the bottom fraction and are not distilled off as losses with the methyl ester.

Second Transesterification Step (Transesterification of the Sterol Esters)

The sterol esters are concentrated in the bottom product of the fatty acid ester distillation process. They are converted into free sterols by transesterification with a short-chain alcohol, preferably methanol, in the presence of a catalyst. Since the transesterification of sterol esters has to take place under more rigorous conditions than the transesterification of partial glycerides, larger quantities of alcohol and catalyst and longer reaction times are necessary.

The quantity of alcohol added is 20 to 100% by weight of the bottom product of the fatty acid ester distillation process. Where methanol is the transesterification reagent, 40 to 60% by weight and more preferably 45 to 55% by weight of the bottom product of the fatty acid ester distillation process are used. Here, too, the catalyst may be a transesterification catalyst.

The reaction preferably takes place over a period of 3 to 10 hours and more particularly 6 to 8 hours at temperatures of 115 to 145° C. and more particularly 120 to 130° C. and under a pressure of 2 to 10 bar and more particularly 3 to 6 bar. Any low-pressure transesterification catalyst may be used as the catalyst. A 30% methanolic sodium methylate solution containing 0.3 to 5% by weight and more particularly 1 to 3% by weight of the fatty acid ester distillation residue is preferably used. The reactor used may be, for example, a stirred batch autoclave.

Alternatively to low-pressure transesterification, the transesterification may again be carried out under elevated pressure. In this case, the reaction takes place over a period of 3 to 6 hours at 200 to 260° C. and under a pressure of 20 to 80 bar. Any high-temperature transesterification catalyst may be used as the catalyst. Zn, Mn, Ti or Ca soaps are preferably used.

Follow-up Processes for Concentrating Free Sterols

Follow-up processes for concentrating sterols are known from German patent applications DE 4228476 and DE 19916034. These include additional steps, such as; catalyst removal and washing with water, crystallization of the sterols, removal of the mother liquor, washing of the crystals conversion of the sterols by melting the crystals and conversion.

In the "conversion of the sterols" process step, the sterols are melted and are either converted into flakes on a flaking roller at 140 to 155° C. or, according to the invention, are converted into droplets by spraying through droplet-forming nozzles into a gravity tower and cooling with cooled and/or dried air flowing in counter-current to such a temperature that they solidify as dust-free beads.

The present invention will now be illustrated in more detail by reference to the following specific, non-limiting examples.

EXAMPLE 1

2600 g of distillation residue from the splitting of sunflower oil (acid value 37) were reacted with 244 g of glycerol and no catalyst in a stirred reaction vessel. After a temperature of 220° C. and a vacuum of 50 mbar had been reached, the sample had an acid value of 5.9. By further reducing the vacuum to 5 mbar and increasing the temperature to 225° C., the acid value fell to 0.2.

EXAMPLE 2

2000 g of distillation residue from the splitting of sunflower oil (acid value 53) were reacted with 174 g of glycerol and 8.6 g of tin(2) isooctoate in a stirred reaction vessel. After a temperature of 215° C. and a vacuum of 7 mbar had been reached, the sample had an acid value of 2.7.

EXAMPLE 3

2700 g of distillation residue from the splitting of soybean oil (acid value 25) were reacted with 157 g of glycerol and no catalyst in a stirred reaction vessel. After a temperature of 220° C. and a vacuum of 50 mbar had been reached, the sample had an acid value of 1.7. After addition of 4.9 g of Simet AP, 4.9 g of Trysil 300 and 4.9 g of water and removal of the sludge by filtration, the reaction product had an acid value of 1.1.

EXAMPLE 4

2110 g of distillation residue from the splitting of soybean oil (acid value 33) were reacted with 114 g of glycerol and 8.9 g of tin(2) isooctoate in a stirred reaction vessel as in Example 1. After a temperature of 215° C. and a vacuum of 7 mbar had been reached, the sample had an acid value of 2.2. US fractions were distilled off with the water.

EXAMPLE 5

1000 g of distillation residue from the splitting of soybean oil (acid value 33) were reacted with 200 g of methanol and 10 g of 50% H3PO3 by boiling under reflux in a stirred reaction vessel. Under a slight excess pressure and at T=135° C., the acid value fell to 4.

EXAMPLE 6

2070 g of the reaction product of Example 4 were transesterified with 310 g of methanol and 31 g of 30% Na methylate solution under mild conditions in an autoclave (8 minutes at 137° C./6 bar). Only 0.8% of free sterols were formed during the mild transesterification. The remaining sterols remained esterified. After expansion of the reaction mixture, 135 g of methanol "flashed off". The reaction mixture was neutralized with 30 g of 50% citric acid and was washed three times with 10% water until neutral. After drying, 983 g of methyl ester were distilled off at 180° C./1 mbar. The methyl ester distillate was free from sterol. No losses of sterol occurred during distillation. The sterol esters remained in the residue II.

130 g of methyl ester distillation residue II were transesterified with 65 g of methanol and 3.2 g of 30% sodium methylate solution for 8 hours at 120° C. and under a low pressure of 5 bar, after which 25 g of methanol were flashed off.

After neutralization of the alkaline catalyst with citric acid and washing of the reaction product with water, 130 g of product containing 7.5% free sterols and 0.04% bound sterols were subjected to crystallization at 15° C. 104 g of mother liquor were removed by filtration.

The filter cake was washed with 65 g of methyl ester, 65 g of methanol and 30 g of water. The dried filter cake contained 93.9% (GC surface area) of free sterols, less than 0.3% of C18 methyl ester and no bound sterols. It contained 1.2% cholesterol, 1.8% brassicasterol, 23.1% campesterol, 15.3% stigmasterol, 48.9% β-sitosterol, 2.2% 5 avenasterol, 1% stigmasterol, 0.3% 7 avenasterol and 0.05% citrostadienol.

EXAMPLE 7

Rapeseed sterols were melted and converted into droplets by spraying through a 650 μm nozzle under a nitrogen pressure of 0.3 bar at 150° C. into a 24 m tall gravity tower at a rate of 1 kg/h/nozzle, cooled with air at 15° C. flowing in counter-current and solidified. Dust-free beads were formed. The final product temperature was 22° C.

EXAMPLE 8

Rapeseed sterols were melted and converted into droplets by spraying through an 800 μm nozzle under a nitrogen pressure of 0.35 bar at 155° C. into a 24 m tall gravity tower at a rate of 3 kg/h/nozzle, cooled with air at 13° C. flowing in counter-current and solidified. Dust-free beads were formed. The final product temperature was 35° C.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process for producing sterols, said process comprising:
   (a) providing a fatty acid production-residue, said residue comprising sterol esters, free fatty acids, and partial glycerides;
   (b) removing the free fatty acids;
   (c) transesterifying the partial glycerides with a lower alcohol in the presence of a basic catalyst under mild transesterification conditions to form fatty acid alkyl esters and glycerol;
   (d) removing excess lower alcohol, the basic catalyst, the glycerol and the fatty acid alkyl esters, to form a bottom product comprising the sterol esters; and
   (e) transesterifying the sterol esters at a temperature of from 115° C. to 145° C. and a pressure of from 2 to 10 bar for a period of from 3 to 10 hours to form free sterols.

2. The process according to claim 1, wherein the fatty acid production-residue is vegetable oil-derived.

3. The process according to claim 1, wherein the fatty acid production-residue comprises a residue derived from an oil selected from the group consisting of soybean oil, sunflower oil, rapeseed oil, coconut oil, palm oil, palm kernel oil, and mixtures thereof.

4. The process according to claim 1, wherein removing the free fatty acids comprises neutralization, precipitation and separation.

5. The process according to claim 4, wherein the free fatty acids are neutralized with a sodium metasilicate to form a precipitate, and the precipitate is separated by filtration.

6. The process according to claim 1, wherein removing the free fatty acids comprises esterifying the free fatty acids with a lower monohydric alcohol to form free fatty acid-based fatty acid alkyl esters, and removing the free fatty acid-based fatty acid alkyl esters with the fatty acid alkyl esters formed in step (d).

7. The process according to claim 1, wherein removing the free fatty acids comprises esterifying the free fatty acids with a polyol to form polyol esters, and transesterifying the polyol esters along with the partial glycerides transesterified in step (c).

8. The process according to claim 7, wherein the polyol comprises glycerol and the free fatty acids are esterified to form free fatty acid-based partial glycerides, and the free fatty acid-based partial glycerides are transesterified along with the partial glycerides transesterified in step (c).

9. The process according to claim 8, wherein esterification of the free fatty acids with glycerol is carried out at a molar ratio of about 1:1, at a temperature of from 215° C. to 230° C., and at a pressure below 1 bar.

10. The process according to claim 1, wherein the transesterification of the partial glycerides under mild conditions is carried out at a temperature of from 90° C to 145° C. and a pressure of from 2 to 10 bar, for a period of from 2 to 20 minutes.

11. The process according to claim 1, wherein the transesterification of the partial glycerides under mild conditions is carried out at a temperature of from 90° C. to 145° C. and a pressure of from 3 to 5 bar, for a period of from 2 to 20 minutes.

12. The process according to claim 8, wherein the transesterification of the partial glycerides under mild conditions is carried out at a temperature of from 90° C. to 145° C. and a pressure of from 2 to 10 bar, for a period of from 2 to 20 minutes.

13. The process according to claim 8, wherein the transesterification of the partial glycerides under mild conditions is carried out at a temperature of from 90° C. to 145° C. and a pressure of from 3 to 5 bar, for a period of from 2 to 20 minutes.

14. The process according to claim 1, wherein the lower alcohol comprises methanol.

15. The process according to claim 1, wherein removing excess lower alcohol comprises allowing expansion until the reaction temperature has cooled to a temperature of from 65° C. to 85° C.

16. The process according to claim 8, wherein the lower alcohol comprises methanol.

17. The process according to claim 8, wherein removing excess lower alcohol comprises allowing expansion until the reaction temperature has cooled to a temperature of from 65° C. to 85° C.

18. The process according to claim 12, wherein the lower alcohol comprises methanol.

19. The process according to claim 12, wherein removing excess lower alcohol comprises allowing expansion until the reaction temperature has cooled to a temperature of from 65° C. to 85° C.

20. The process according to claim 1, wherein the removal of the basic catalyst comprises the addition of an aqueous solution of an acid, precipitation of the catalyst and separation of the precipitate.

21. The process according to claim 1, wherein the fatty acid alkyl esters are removed by distillation.

22. The process according to claim 21, wherein the distillation is carried out at a temperature of from 170° C. to 200° C. and a pressure of from 1 to 5 mbar.

23. The process according to claim 14, wherein the fatty acid alkyl esters are removed by distillation.

24. The process according to claim 23, wherein the distillation is carried out at a temperature of from 170° C. to 200° C. and a pressure of from 1 to 5 mbar.

25. The process according to claim 16, wherein the fatty acid alkyl esters are removed by distillation.

26. The process according to claim 25, wherein the distillation is carried out at a temperature of from 170° C. to 200° C. and a pressure of from 1 to 5 mbar.

27. The process according to claim 18, wherein the fatty acid alkyl esters are removed by distillation.

28. The process according to claim 27, wherein the distillation is carried out at a temperature of from 170° C. to 200° C. and a pressure of from 1 to 5 mbar.

29. The process according to claim 1, wherein the transesterification of the sterol esters is carried out at a temperature of from 120° C. to 130° C. and at a pressure of from 3 to 6 bar, for a period of from 4 to 8 hours.

30. The process according to claim 1, further comprising purification of the free sterols via crystallization and washing.

31. The process according to claim 1, further comprising subjecting the free sterols to droplet formation via melting, spraying through droplet-forming nozzles, and solidification via cooling with countercurrent airflow in a gravity tower, to form dust free spherical particles.

32. A process for producing sterols, said process comprising:

(a) providing a fatty acid production-residue derived from an oil selected from the group consisting of soybean oil, sunflower oil, rapeseed oil, coconut oil, palm oil, palm kernel oil, and mixtures thereof, said residue comprising sterol esters, free fatty acids, and partial glycerides;

(b) esterifying the free fatty acids with glycerol to form free fatty acid-based partial glycerides;

(c) transesterifying the partial glycerides and the free fatty acid-based partial glycerides with methanol in the presence of a basic catalyst at a temperature of from 90° C. to 145° C. and a pressure of from 2 to 10 bar, for a period of from 2 to 20 minutes, to form fatty acid methyl esters and glycerol;

(d) removing excess methanol, the basic catalyst, and the glycerol, and distilling off the fatty acid methyl esters at a temperature of from 170° C. to 200° C. and a pressure of from 1 to 5 mbar, to form a bottom product comprising the sterol esters; and (e) transesterifying the sterol esters at a temperature of from 115° C. to 145° C. and a pressure of from 2 to 10 bar for a period of from 3 to 10 hours to form free sterols.

* * * * *